(12) United States Patent
Liou

(10) Patent No.: US 6,217,323 B1
(45) Date of Patent: *Apr. 17, 2001

(54) DENTAL DISTRACTOR

(76) Inventor: Eric Jein-Wein Liou, No. 199, Tun-Hwa North Rd., Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 09/376,326

(22) Filed: Aug. 18, 1999

(51) Int. Cl.[7] ........................................ A61C 3/00
(52) U.S. Cl. ................... 433/18; 433/7; 433/17
(58) Field of Search .................... 433/18, 17, 7

(56) References Cited

U.S. PATENT DOCUMENTS

| | | | |
|---|---|---|---|
| 618,105 | * | 1/1899 | Knapp ........................ 433/7 |
| 678,452 | * | 7/1901 | Angle ........................ 433/7 |
| 4,424,031 | * | 1/1984 | Dahan ........................ 433/18 |
| 5,645,423 | * | 7/1997 | Collins, Jr. ................. 433/18 |

* cited by examiner

Primary Examiner—John J. Wilson
(74) Attorney, Agent, or Firm—Dougherty & Troxell

(57) ABSTRACT

An orthodontic dental distractor for rapid orthodontic tooth movement into a fresh extraction socket. The device includes a screw bar and a screw nut fixedly engaged with one end of the screw bar, a first joint engageable with one end of the screw bar next to the screw nut and a first hook engageable with a canine band mounted on a canine. A second joint is engageable with another end of the screw bar and has a second hook engageable with a molar band mounted on a molar. By turning the screw nut, the screw bar will move the first joint towards the second joint, thus moving the canine rearward toward the molar.

3 Claims, 6 Drawing Sheets

DENTAL DISTRACTOR

BACKGROUND OF THE INVENTION

1. Field of the Invention

This invention relates to a dental distractor and particularly to a dental distractor for correcting severe front teeth crowding and protrusion in orthodontic treatment.

2. Description of the Prior Art

Conventional orthodontic treatment for severe anterior teeth crowding or protrusion generally includes the following five steps:

1. Extracting the first premolars.
2. Initial teeth leveling by using orthodontic brackets and arch wires. Depending on the alignment of teeth, this step lasts about three to six months.
3. Retracting canine backward into the first premolar extraction space for anterior teeth. This step lasts about four to six months for children and seven to eight months for adults.
4. Retracting anterior teeth to level the protruding teeth. This step lasts about six months.
5. Fine adjustment of occlusion and tooth angulation. This step takes about three to six months.

Total orthodontic treatment time will take one and a half to two years. It is too long a time for most patients. It is not esthetic to wear braces for such a long period and it is very burdensome for the patients to maintain their oral hygiene as well. It also is very inconvenient and time-consuming for the patients to visit orthodontist's office over such a long period. Two major steps make the period of orthodontic treatment long. They are the step 3 (canine retraction) and step 4 (anterior retraction), which take a whole year in total.

FIGS. 1 and 2 show a conventional method for canine reaction after first premolar extraction with an elastic power chain. The first molar is engaged with a molar band 12 and a bracket 121 welded on the buccal surface thereof. The canine 3 is engaged with a canine band 32 and a bracket 321 welded on the buccal surface thereof. An elastic power chain 2 is engaged between the brackets 121 and 321. The elastic power chain 2 is made of synthetic rubber formed in a chain manner including a plurality of loops 21. The chain is cut to a length desired and has the two end loops engaging respectively with the brackets. Through the elastic force of the elastic power chain 2, the canine 3 may be pulled gradually toward the first molar 2 and a space being left behind the canine. The rubber of the power chain 2 tends to lose elasticity after soaking in saliva for a period of time. It usually takes more than six months to retract a canine into a desirable position (i.e., moving the canine rearward for 4–5 mm). It takes too much time and prolongs the total treatment time.

FIG. 3 illustrates another conventional method for canine retraction disclosed in U.S. Pat. No. 5,873,715 which is disclosed by the same inventor of the present invention. The method illustrated in U.S. Pat. No. 5,873,715 uses a dental distractor 4. The dental distractor 4 includes a distractor head 41, a movable joint 42 and a screw 43. There is a molar band 121a mounted on the first molar 1. The molar band 12a has buccal sheaths 121a welded on buccal surface. The buccal sheaths 121a have two spaced cylindrical bores located therein. The canine 3 has a canine band 32a mounted thereon. On the buccal surface of the band 32a, there is a reversed U-shaped hook 321a fixed thereon.

Referring to FIGS. 3 and 4, the distractor head 41 includes an engaging end 411 which is substantially a C-shaped bar. The engaging end 411 has an upper bar 4114 which has two legs 41142 engageable with the cylindrical bores of the buccal sheaths 121a. The engaging end 411 further has a lower bar 4112 connecting with one end of a sliding bar 415. A screw seat 413 is fixed on the sliding bar 415 and has a first screw bore 4132 engageable with a screw bar 432.

Referring to FIG. 5, the movable joint 42 includes a connecting screw 421 with a slot 4212 and a cap 4213. The cap 4213 is to secure the hook 321a in the connecting screw 421. There is a second screw bore 423 in the movable joint 42 enagageable with a screw bar 432 of the screw 43 and a sliding bore 425. The sliding bar 415 slidably runs through the sliding bore 425. The screw 43 has a screw head 434 at one end thereof.

When a patient is undergoing rapid orthodontic treatment for correcting severe anterior crowding or protrusion, the canine 3 has to be moved backward with the distractor immediately after the first premolar extraction and before the new alveolar bone is generated. The molar band 12a is mounted on the first molar 1 and the canine band 32a is mounted on the canine 3 before the first premolar extraction. Immediately after the first premolar extraction, the distractor head 41 is mounted on the molar band 12a by engaging the legs 41142 into the buccal sheath 121a. The movable joint 42 is engaged with the canine band 32a by inserting the hook 321a into the slot 4212. Then the screw seat 413 is engaged with the movable joint 42 by turning the screw head 434. For each turn or a fractional turn, the screw head 434 will drive the movable joint 42 back a definite distance toward the screw seat 413, thus achieve the object of moving the canine 3 rapidly. The distractor of this invention may be made of high strength alloy with stable property and biocompatibility.

By following orthodontist's instructions, patients may turn the screw head 434 easily by using a simple tool without going to orthodontist's office. The force generating by the screw 43 and the movable joint 42 is more effective than the elastic power chain.

The following is the general procedures of using this method to perform rapid orthodontic tooth movement:

1. Putting on orthodontic brackets for initial alignment and leveling anterior teeth for one or two months.
2. Extracting first premolars and putting on dental distractors to move the canines within three weeks.
3. Retracting anterior teeth backward for about 4–5 months.
4. Fine adjusting the occlusion and tooth angulation.

Although the second method (i.e., U.S. Pat. No. 5,873, 715) disclosed above may speed up orthodontic treatment, it has the problem of having too complicated and too bulky a structure. It is particularly annoying to put it in the month which is delicate and sensitive. It is prone to hurt mucous membranes and even causes oral ulcers.

SUMMARY OF THE INVENTION

It is an object of this invention to provide a dental distractor that overcomes the problem of long orthodontic treatment time resulting from the conventional method of using elastic power chain which loses elasticity after soaking in saliva and offers faster orthodontic treatment. The dental distractor has simpler structure and smaller size than the bulky and complicated conventional dental distractor for patients to use more conveniently and comfortably.

The dental distractor according to this invention is mainly for rapid orthodontic tooth movement after the first premolar extraction is done. It includes a molar band mounted on a molar, a canine band mounted on canine, a first joint means, a second joint means and a screw bar means. The molar band has a molar triple tube located on a buccal side and the canine band has a canine triple tube located on another buccal side thereof. The second joint means includes a second hook engageable with the molar triple tube and a second joint engageable with a screw bar of the screw bar means. The first joint has a first hook engageable with the canine triple tube and a first joint engageable with the screw bar. There is a screw nut fixedly engageable with one end of the screw bar. Turning the screw nut, the first joint means will be moved toward the second joint means and consequently moving the canine rearward toward the first molar.

BRIEF DESCRIPTION OF THE DRAWINGS

The following description and draws show the invention, as well as its many advantages.

DETAILED DESCRIPTION OF THE PREFERRED EMBODIMENT

Figure 1:
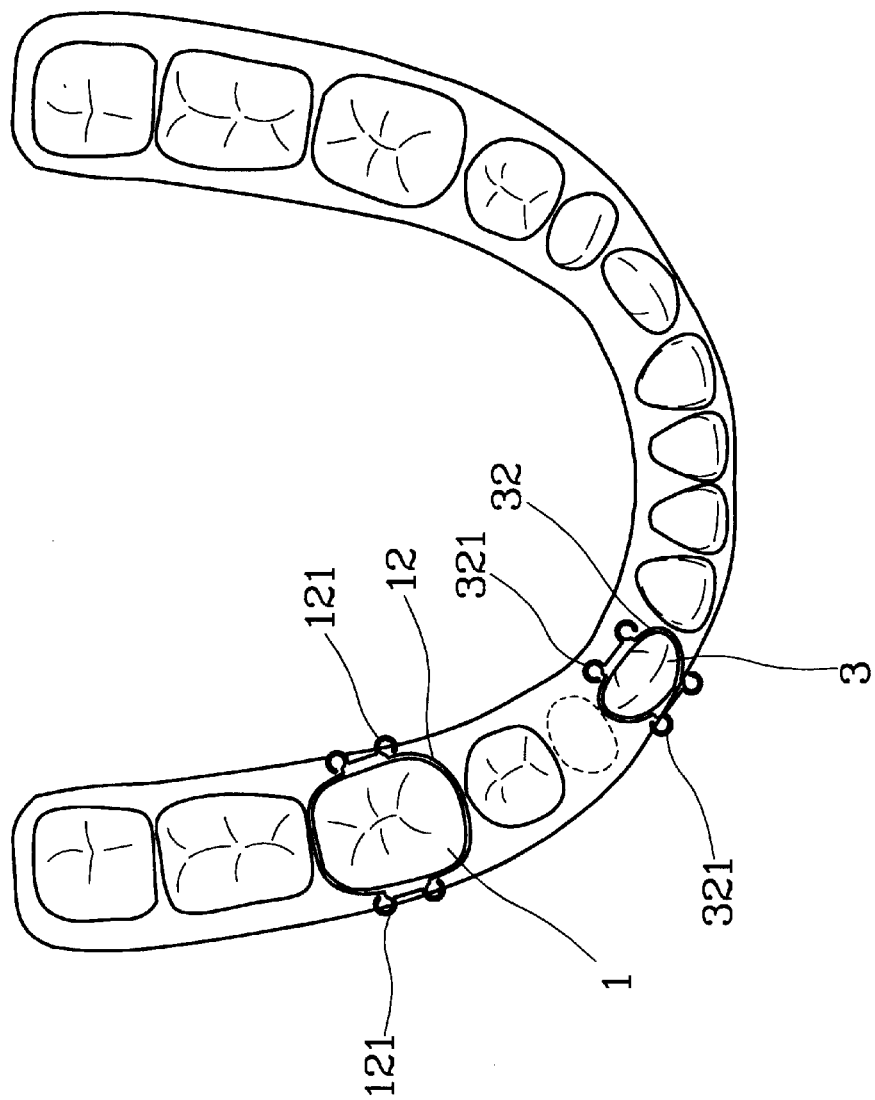
FIG. 1 is a partial top view of a conventional device for canine retraction.
Figure 2:
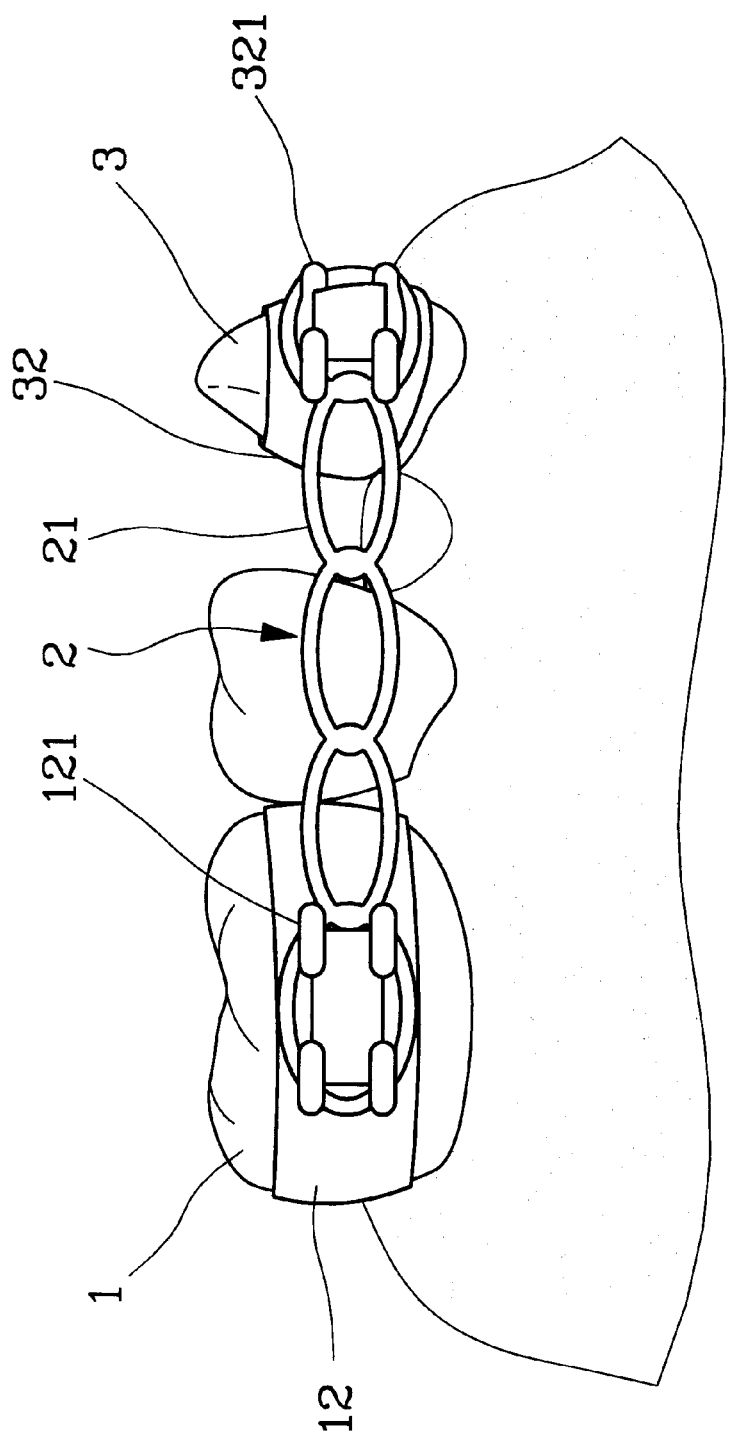
FIG. 2 is a front view of a conventional device for canine retraction shown in FIG. 1.
Figure 3:
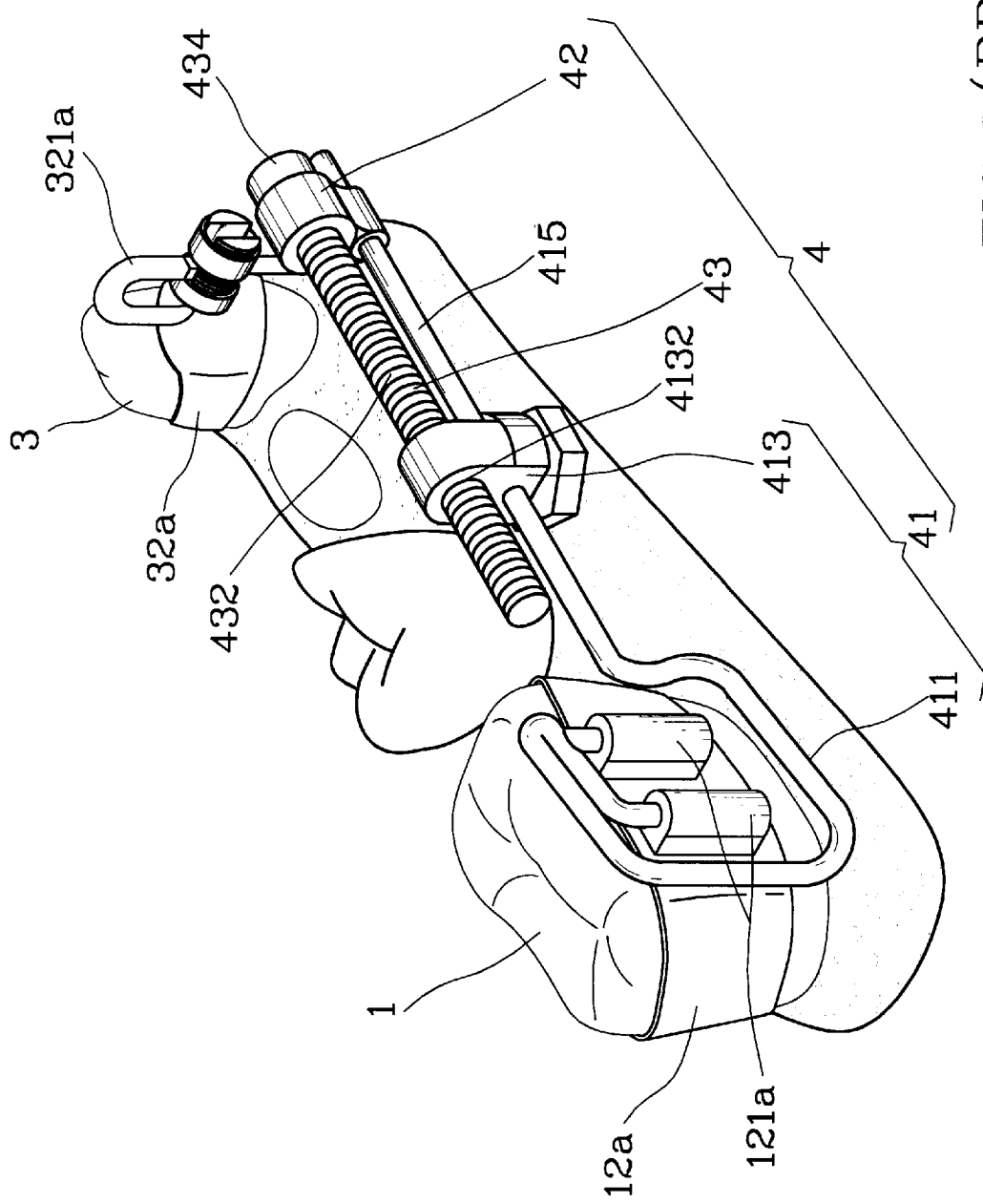
FIG. 3 is a perspective view of another prior art method for canine retraction.
Figure 4:
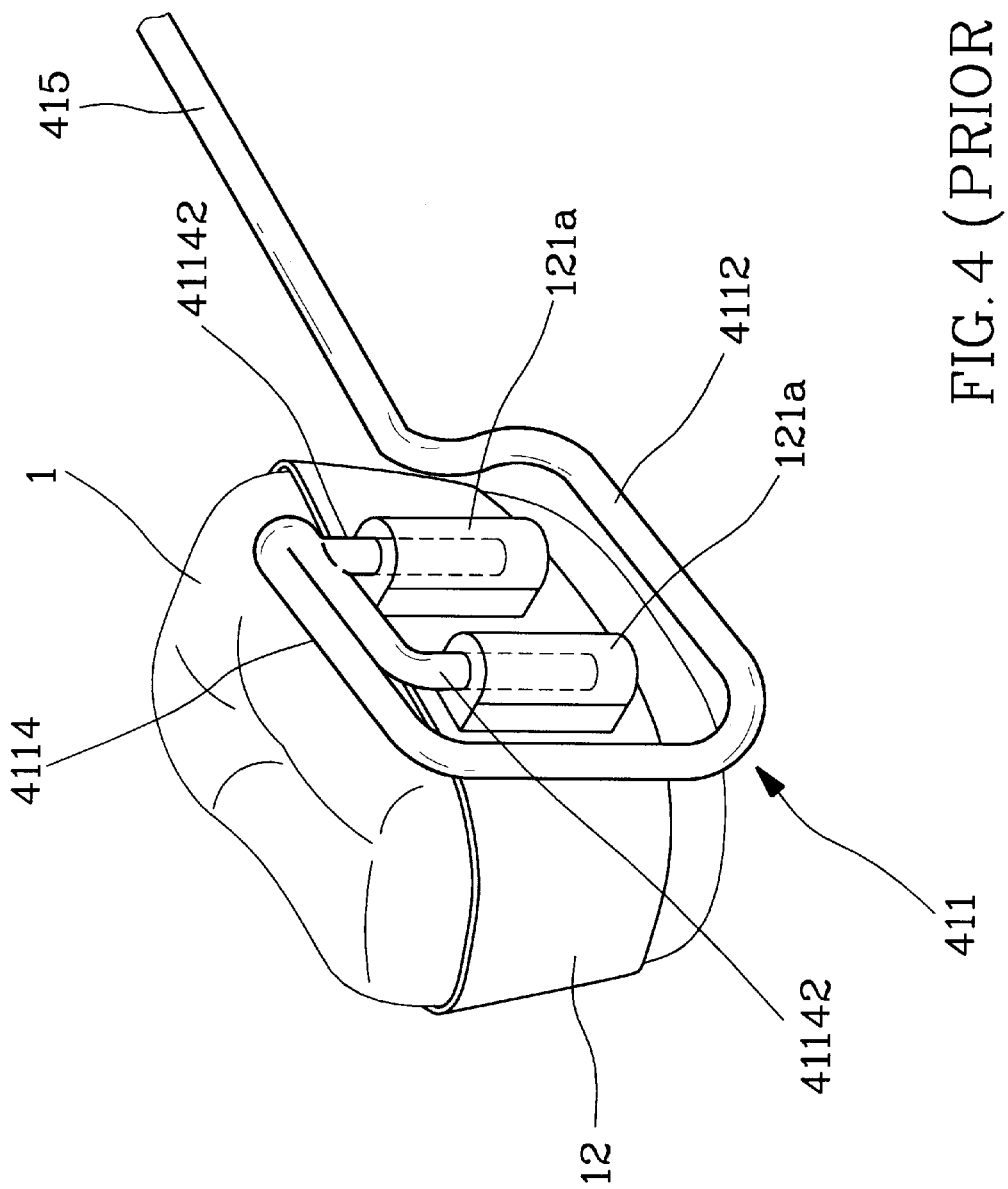
FIG. 4 is a fragmentary perspective view of the device shown in FIG. 3.
Figure 5:
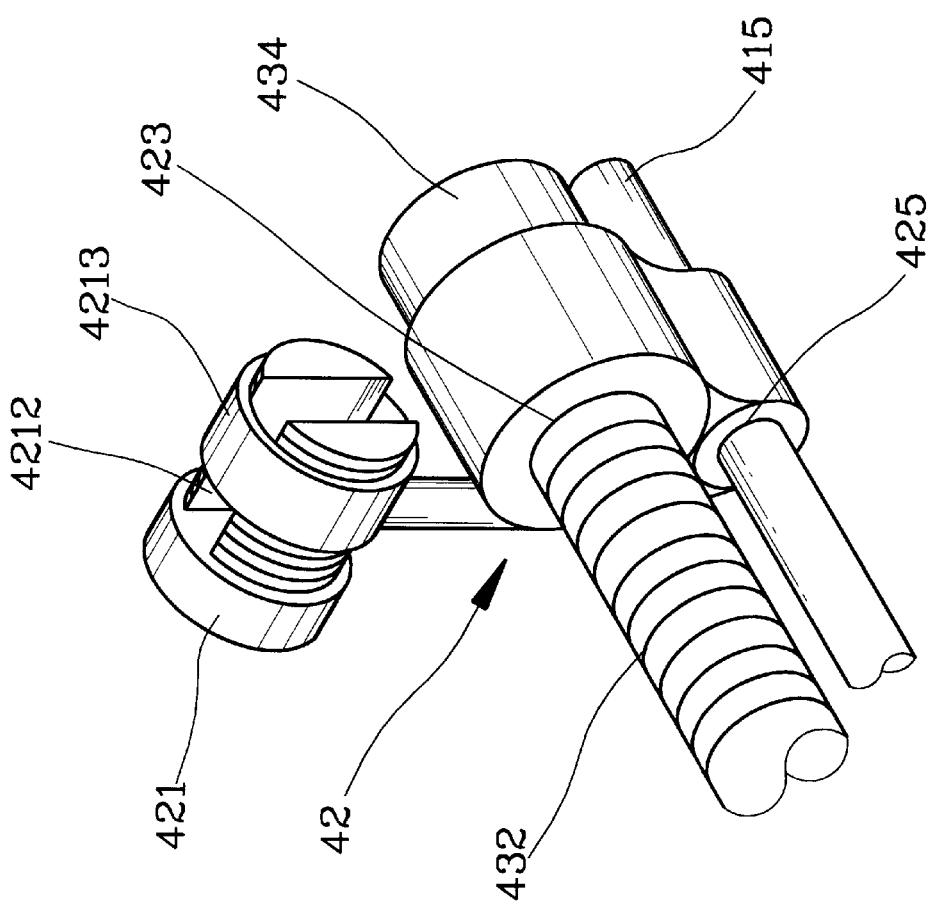
FIG. 5 is another fragmentary perspective view of the device shown in FIG. 3.
Figure 6:
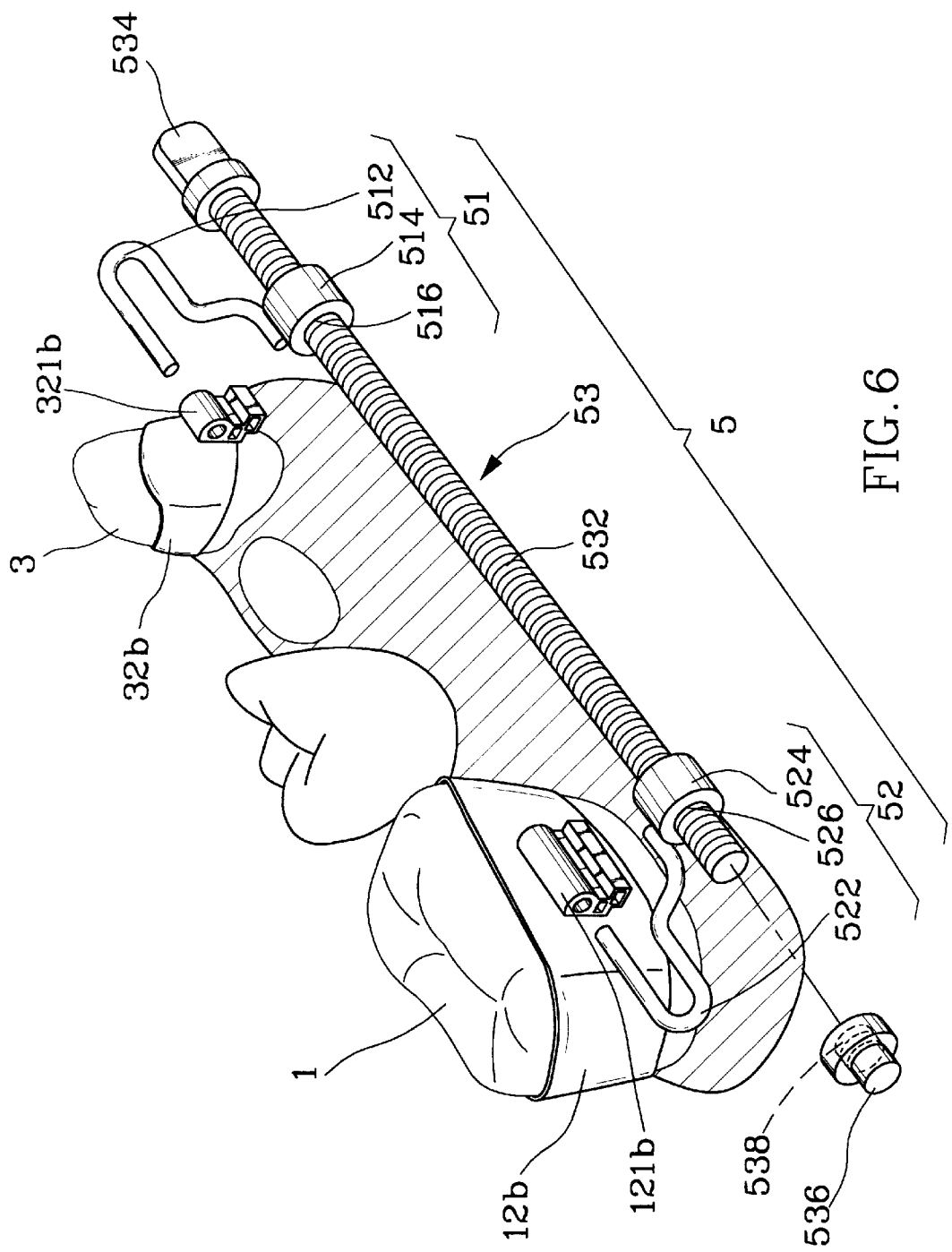
FIG. 6 is a perspective view of the device of this invention.

Referring to FIG. 6, the dental distractor 5 according to this invention is mainly for moving the canine 3 rearward after the first premolar has been extracted. It includes a molar band 12b for mounting on a molar 1, a canine band 32b for mounting on the canine 3, a first joint means 51 engageable with one end of a screw bar 532 of a screw bar means 53, and a second joint means 52 engageable with another end of the screw bar 532.

The molar band 12b has a molar triple tube 121b formed at a buccal side. The canine band 32b has a canine triple tube 321b formed at another buccal side. The first joint means 51 includes a C-shaped first hook 512 which opens toward the inside and which has one end engageable with the canine triple tube 321b and another end fixedly engaged with a first joint 514. The second joint means 52 includes a C-shaped second hook 522 which opens toward the inside and which has one end engageable with the molar triple tube 121b and another end fixedly engaged with a second joint 524.

The screw bar means 5 include the screw bar 532 and a screw nut 534 fixedly mounted at one end of the screw bar 532. An additional screw nut 536 having a screw hole 538 therein can also be detachably engaged at the other end of the screw bar 532. The screw bar 532 has one end penetrating through a bore 516 formed in the first joint 514 which is located next to the screw nut 534 and another end engageable with a screw hole 526 formed in the second joint 524.

When in use, the first hook 512 is engaged with the canine sheath 321b, and the second hook 522 is engaged with the molar sheath 121b, then the screw nut 534 is turned a number of turns or a fraction of a turn as desired. The screw nut 534 will push against the first joint 514. Consequently, turning the screw nut 534 will force the screw bar 532 to move the second joint 524 toward the first joint 514 which in turn will move the canine 3 rearward a distance. The turning of the screw nut 534 may be done by the patient following the orthodontist's instructions. It may be done simply and conveniently. It is stronger than the conventional rubber made power chain and may move the canine by 6–7 mm within three weeks.

The dental distractor 5 according to this invention may be made of alloy which has great strength and stable properties without reaction with saliva. It is safer to use. The whole device may be made smaller size than the conventional one. It thus makes the patient more comfortable without the risk of hurting or festering. The whole device has smaller number of parts and a simpler structure. Thus, it is easier to made at a lower cost.

It may thus be seen that the objects of the present invention set forth herein, as well as those made apparent from the forgoing description, are efficiently attained. While the preferred embodiment of the invention has been set forth for purpose of disclose, modifications of the disclosed embodiment of the invention as well as other embodiments thereof may occur to those skilled in the art. Accordingly, the appended claims are intended to cover all embodiments which do not depart from the spirit and scope of the invention.

What is claimed is:

1. A dental distractor for rapid orthodontic tooth movement after tooth extraction, comprising:

a canine band for mounting on a canine and having a canine triple tube on a buccal side thereof, the canine triple tube having a horizontal first bore;

a molar band for mounting on a molar and having a molar triple tube on a buccal side thereof, the molar triple tube having a horizontal second bore;

a first joint device including a first hook engaged with the first bore of the canine triple tube and a first joint having a through hole formed therein, wherein the first hook is C-shaped with a first end portion engaged with the first bore and a second end portion fixedly connected to the first joint;

a second joint device including a second hook engaged with the molar band and a second joint having a screw hole formed therein, wherein the second hook is C-shaped with a first end portion engaged with the second bore and a second end portion fixedly connected to the second joint, the C-shapes of the first and second hooks opening towards each other; and a screw bar having a first end passing through the through hole of the first joint and a second end engaged with the screw hole of the second joint, and a screw nut fixedly mounted on said first end of the screw bar adjacent to the first joint;

wherein the first joint device is moved toward the second joint device when the screw nut is turned for moving the canine rearward.

2. The dental distractor of claim 1, wherein the dental distractor is made of a stable alloy.

3. The dental distractor of claim 1, further comprising a second screw nut having a screw hole therein detachably engaging said second end of the screw bar.

* * * * *